United States Patent
Varghese et al.

(10) Patent No.: US 9,676,059 B2
(45) Date of Patent: Jun. 13, 2017

(54) LASER HAIR CUTTER

(71) Applicant: KONINKLIJKE PHILIPS N.V., Eindhoven (NL)

(72) Inventors: Babu Varghese, Eindhoven (NL); Rieko Verhagen, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/418,198

(22) PCT Filed: Jul. 26, 2013

(86) PCT No.: PCT/IB2013/056154
§ 371 (c)(1),
(2) Date: Jan. 29, 2015

(87) PCT Pub. No.: WO2014/020512
PCT Pub. Date: Feb. 6, 2014

(65) Prior Publication Data
US 2015/0298254 A1 Oct. 22, 2015

Related U.S. Application Data

(60) Provisional application No. 61/677,506, filed on Jul. 31, 2012.

(51) Int. Cl.
*B23K 26/04* (2014.01)
*B23K 26/06* (2014.01)
(Continued)

(52) U.S. Cl.
CPC ............ *B23K 26/04* (2013.01); *A61B 18/203* (2013.01); *B23K 26/0665* (2013.01); *B23K 26/38* (2013.01); *A61B 2018/00476* (2013.01)

(58) Field of Classification Search
CPC .......... A61B 2018/20; A61B 2018/004; A61B 18/20; B23K 26/04; B23K 26/0665; B23K 26/38; B23K 26/042
(Continued)

(56) References Cited

U.S. PATENT DOCUMENTS 5,993,440 A * 11/1999 Ghassemi ............... B26B 19/00
30/41.5
6,149,645 A * 11/2000 Tobinick ............... A61B 18/203
606/10
(Continued)

FOREIGN PATENT DOCUMENTS

JP 06302900 A 10/1994
JP 2005177788 A 7/2005
(Continued)

OTHER PUBLICATIONS

Kharin A, Varghese B, Verhagen R, Uzunbajakava N; Optical properties of the medulla and the cortex of human scalp hair. J. Biomed. Opt. 0001;14(2):024035-024035-7.*
(Continued)

*Primary Examiner* — Lynsey Crandall
*Assistant Examiner* — Amanda Steinberg

(57) ABSTRACT

A device for cutting hair is disclosed that includes a laser beam generator (2) and a polarisation controller (6) configured to polarise the laser beam (10) and substantially align the polarisation of the laser beam with a longitudinal axis of a hair to be cut. Also disclosed is a method of cutting hair using a laser beam to cut hair. The method including generating and polarising the laser beam to substantially align the polarisation of the laser beam with a longitudinal axis of a hair to be cut.

13 Claims, 2 Drawing Sheets

(51) Int. Cl.
*B23K 26/38* (2014.01)
*A61B 18/20* (2006.01)
*A61B 18/00* (2006.01)

(58) Field of Classification Search
USPC .................................................. 606/9
See application file for complete search history.

(56) References Cited

U.S. PATENT DOCUMENTS

| | | | |
|---|---|---|---|
| 7,108,690 B1* | 9/2006 | Lefki | A61B 18/203 606/10 |
| 7,582,082 B2* | 9/2009 | Van Hal | A61B 18/203 606/10 |
| 2008/0215038 A1* | 9/2008 | Bakker | A61B 18/203 606/9 |
| 2008/0255548 A1* | 10/2008 | Van Hal | A61B 18/203 606/10 |
| 2010/0063491 A1* | 3/2010 | Verhagen | A61B 5/0066 606/9 |
| 2010/0069897 A1* | 3/2010 | Spikker | H01S 3/101 606/9 |
| 2011/0022039 A1* | 1/2011 | Spikker | A61B 18/203 606/9 |
| 2012/0002204 A1* | 1/2012 | Varghese | G01N 21/23 356/369 |

FOREIGN PATENT DOCUMENTS

| | | |
|---|---|---|
| JP | 2006122988 A | 5/2006 |
| WO | 9216338 A1 | 10/1992 |
| WO | 9533600 A1 | 12/1995 |
| WO | 9907438 A1 | 2/1999 |
| WO | 2005102153 A1 | 11/2005 |
| WO | 2007039854 A1 | 4/2007 |
| WO | 2010106480 A1 | 9/2010 |

OTHER PUBLICATIONS

N. Lechocinski and S. Breugnot, "Fiber orientation measurement using polarization imaging", Journal of Cosmetic Science, vol. 62, No. Mar./Apr. 2011, pp. 85-100, 2011.*
L. Habbema, R. Verhagen, R. Van Hal, Y.Liu, B. Varghese, "Minimally invasive non-thermal laser technology using laser-induced optical breakdown for skin rejuvenation", Journal of Bio-photonics, (2011).
3. R.Dorn, S.Quabis and G.Leuchs, "Shaper focus for a radially polarized light beam," Physical Review Letters, 91(23), 2003.
G.M. Lermna and U. Levy, "Effect of radial polarization and apodization on spot size under tight focusing conditions," Optics Express, 16(7), 2008.
Babu Varghese*, Rieko Verhagen, Qiangqiang Tai, Altaf Hussain, Clemence Boudot, and Natallia Uzunbajakava, "Contrast improvement in scattered light confocal imaging of skin birefringent structures by depolarization detection," J. Biophotonics 1-9 (2011) / DOI 10.1002/jbio.201100063.

* cited by examiner

LASER HAIR CUTTER

This application is the U.S. National Phase application under 35 U.S.C. §371 of International Application No. PCT/IB2013/056154, filed on Jul. 26, 2013, which claims the benefit of U.S. Provisional Application No. 61/677,506 filed on Jul. 31, 2012. These applications are hereby incorporated by reference herin.

FIELD OF THE INVENTION

This invention relates to a device for cutting hair using a laser beam.

BACKGROUND OF THE INVENTION

It is known to use a laser beam to cut hairs in a laser shaver, cutter or trimmer. A laser beam is generated and directed towards hair which is severed by optical absorption; hair absorbs the electromagnetic energy of the incident laser beam which vaporises the hair.

A problem with existing laser cutting devices is that only a part of the energy of the laser beam is absorbed by the hairs so the power of the laser beam must be increased to ensure that hairs are severed. However, the skin exposure to the laser beam and to heat created by the laser beam will also increase, causing irritation to the skin. Furthermore, the increased power requirements will increase electricity consumption meaning if the shaver is battery powered, battery life is reduced. Also, higher energy lasers can cause damage to the optical components of the device.

SUMMARY OF THE INVENTION

It is an object of the invention to provide a device for cutting hair using a laser beam which substantially alleviates or overcomes the problems mentioned above.

According to the present invention, there is provided a device for cutting hair using a laser beam, having a laser beam generator and a polarisation controller configured to polarise the laser beam and substantially align that polarisation with a longitudinal axis of a hair to be cut.

Aligning the polarisation of the laser beam with the hair will orientate the energy of the electromagnetic waves of the laser beam in the same direction and increase the cutting effectiveness of the laser beam. The hair will absorb a higher proportion of the laser beam energy and therefore the overall power of the laser beam can be reduced.

Preferably, the polarisation controller is configured to orientate the polarisation of the laser beam such that the orientation of an electric field component of the laser beam is substantially parallel to a longitudinal axis of a hair to be cut.

Orientating the laser beam polarisation to align with the longitudinal axis of a hair will increase the attenuation coefficient when the laser beam interacts with that hair. The laser beam polarisation may be orientated to maximise the attenuation of the laser beam at the cortex or medulla of a hair to be cut. Therefore, the hair will absorb more of the energy of the laser beam and less of the energy of the laser beam will interact with the skin, which will reduce irritation and damage caused to the skin. Also, the overall power of the laser beam may be reduced as less of the laser beam energy is wasted. This increased cutting efficiency may lead to reduced power consumption and therefore, if the device is battery powered, battery life can be lengthened. Furthermore, the decreased laser power may reduce skin irritation as well as damage caused to optical components. Increased cutting efficiency may also allow the device to be moved over the skin at a higher speed without reducing cutting performance.

In one embodiment, the polarisation controller may be a half-wave plate. A half-wave plate works by retarding some wave components of unaligned waves which rotates the waves such that the laser beam is polarised. No part of the beam is blocked or absorbed so the laser beam energy is maintained. This allows the overall power of the laser beam and power consumption to be reduced, which also reduces skin irritation. The reduced overall power of the laser beam reduces damage to optical components. Increased cutting efficiency obtained by polarizing the whole of the laser beam in the preferred direction may allow the device to be moved over the skin at a higher speed without reducing cutting performance when compared to the situation in which the laser beam did not undergo any polarization.

In another embodiment, the polarisation controller may comprise a polarising filter. A polarising filter can be configured to block waves of the laser beam orientated in an undesirable orientation so that the light that passes through is orientated in a single direction which can be aligned with the hair to be cut. Aligning the polarisation orientation with the hair using a polarising filter will reduce the skin irritation and damage because more of the laser beam energy will be absorbed by the hair and less by the skin of a user.

The device may also include a hair-skin manipulator that contacts the skin of a user and manipulates hair into an orientation suitable for cutting as the device is moved over the skin.

The hair-skin manipulator acts to move the hairs so that each of the hairs is orientated in a similar direction that is also suitable for the laser beam to sever— based on the orientation of the polarisation of the beam. This may include making the hairs stand upright, at a right angle to the skin.

The polarisation controller may have a fixed position which corresponds to an average hair orientation as the hair-skin manipulator moves over the skin of a user and manipulates hairs.

If the polarisation controller has a fixed position then the hair-skin manipulator should move the hairs into an orientation that is suitable for this particular polarisation orientation. The arrangement is simple but effective as most hairs will pass through the shaver in a similar orientation, allowing the polarisation controller to be fixed in a position that is appropriate for the majority of hairs, improving the performance of the device.

The device may further comprise a hair detection module including an optical imaging device configured to detect hair to be cut and determine an orientation of that hair.

The hair detective module may be configured to detect the orientation of individual hairs or an average orientation of the hairs to be cut. In this way, the optimum polarisation orientation can be determined to reduce the required laser beam power.

The polarisation controller may be configured to change the polarisation orientation in response to the detected angle of a hair in the cutting zone.

Changing the polarisation orientation of the laser beam to match the detected hair orientation will further improve performance by ensuring that more hairs are severed with optimum, or nearly optimum, attenuation coefficient, reducing the required laser beam energy.

The polarisation controller may be integrated with the laser beam generator and the orientation of the polarisation of the laser beam is changed by rotating the laser beam generator and the polarisation controller In this way, the device would be more compact and rotation of the integral laser beam generator and polarisation controller is simple and effective.

The laser beam generator may be configured to generate a series of laser pulses.

Each laser pulse can have reduced energy and the cumulative effect of several pulses will cause the hair to be severed. Reducing the energy of the laser beam will further reduce irritation caused to the skin.

The laser beam generator may be configured to generate pulses with an inter-pulse delay that is less than a thermal relaxation time of the hair.

If each pulse arrives before the temperature of the hair recovers from the last pulse then the optical absorption of each pulse will increase the temperature of the hair. Eventually, the cumulative effect of several pulses will cause the hair to be severed.

The laser beam generator may be configured to operate at an absorption wavelength of a hair to be cut. In this way, the laser beam will interact more with the hair and less with the skin, which will reduce irritation and increase cutting effectiveness.

The optical system may be configured to generate a plurality of laser beams, the polarisation of which is aligned with a longitudinal axis of a hair to be cut.

A device with multiple laser beams will ensure more hairs are cut and the device can cover a larger area with a single pass.

According to another aspect of the invention, there is provided a method of using a laser beam to cut hair including generating a laser beam, polarising the laser beam and substantially aligning the polarisation of the laser beam with a longitudinal axis of a hair to be cut.

The laser beam may be polarised such that an electric field component of the laser beam is substantially parallel to a longitudinal axis of a hair to be cut. These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
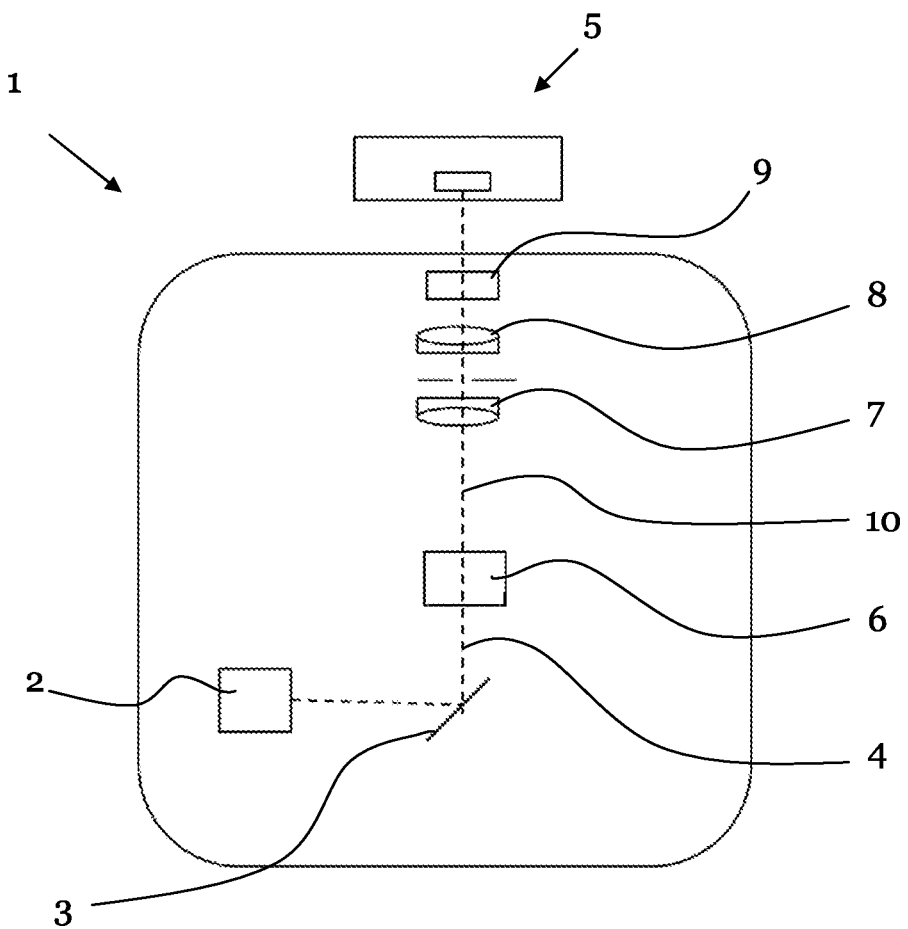
FIG. 1 shows a schematic view of a test rig for an optical system for a device for cutting hair using a laser beam.

A laser shaver may comprise an optical system that includes a laser beam generator that directs a laser beam towards a user's hair and/or skin. The laser shaver can be moved across the user's skin so that hairs on the skin are exposed to the laser beam and severed by optical absorption. A spacer with a plurality of openings may be used to maintain the desired spacing between the cutting zone and the user's skin, thereby determining the cutting height and the remaining hair length. The cutting height may be adjustable to change the function of the shaver to a trimmer or cutter that does not aim to minimise remaining hair length but to leave some hair after use, for example a beard trimmer.

When the laser shaver is moved over the user's skin and the hair is exposed to the laser beam, the hair absorbs at least some of the electromagnetic energy of the laser beam which causes the hair to be vaporised and severed. This cutting process is based on optical absorption, or photothermolysis and the wavelength of the laser beam may be optimised to match the peak absorption wavelength of the hair to be severed. This selective photothermolysis targets the hairs by tuning the wavelength of the laser beam to interact with the hair, based on the colour of the hair, but not interact with skin and other surrounding features, thereby avoiding damage and irritation of the skin.

Optical absorption is also called attenuation and the magnitude of attenuation is dependent on several factors, such as the hair pigment, thickness, orientation and beam energy. Some of these factors determine the magnitude of the attenuation coefficient. A higher attenuation coefficient means that a higher proportion of the laser beam's energy is absorbed by the hair, so that the hair can be severed at a reduced total laser power which reduces skin irritation and extends battery life.

Hair comprises three main components: the medulla, which is the innermost core of a hair; the cortex, which is a medial layer; and, the cuticle, which is the outermost layer of hair and formed of overlapping cells. The pigment, thickness, strength and optical properties of hair vary according to different species and, within humans, between individuals. In order to sever a hair using a laser beam all of these layers must be vaporised. These different layers will have different optical absorption characteristics and so the wavelength and power of the laser beam will need to be selected to ensure that all the components of the hair are severed at the operating point of the laser beam in a shaver.

A laser beam comprises transverse electromagnetic waves, each formed of two perpendicular field components that propagate in the same direction—an electric field and a magnetic field. The electric and magnetic components of an electromagnetic wave will always be perpendicular to each other, however, they may be in any orientation and that orientation may be fixed or it may change as the wave propagates, for example a twisting or circular polarised wave.

The alignment of the two components with respect to a target object to be cut, such as a hair, will affect the magnitude of attenuation and therefore the beam power required to sever that hair. In other words, the orientation of the electric and magnetic field components within the laser beam influences the attenuation coefficient when that beam interacts with the object. Therefore, the magnitude of attenuation is dependent on the polarisation orientation and this orientation can be tuned to increase the magnitude of the attenuation and improve the effectiveness and efficiency of the laser cutting. The orientation of the electric field components may also be controlled so that the waves are uniformly aligned and have a fixed orientation as the beam propagates. This gives more control over the interaction between the laser beam and the hair and also allows the effective focus depth to be altered without altering the orientation of the electric field in the cutting zone.

As explained, the attenuation coefficient when a laser beam interacts with an object is dependent on several factors and this includes the orientation of the electric field components of the electromagnetic waves of the laser beam in relation to the object to be cut. This effect is accentuated when the target object has an elongate shape, for example hair, as waves aligned perpendicularly to the main axis of the elongate object will experience less attenuation and transfer less energy to the object. Therefore, the performance of a laser shaver can be improved by aligning the electrical component of the incident laser beam with the elongate axis of the hair to be cut, so that a higher proportion of the laser beam's energy is absorbed by the hair. In other words, the polarisation of the laser beam can be tuned to increase the attenuation coefficient and therefore improve the effectiveness and efficiency of the cutting process.

Experimentation was carried out to quantify the increased attenuation coefficient after tuning the polarisation of the laser beam. Table 1 below shows the results of this experiment which was carried out on the test rig shown schematically in FIG. 1.

The test rig 1 comprises a laser beam generator 2, such as a diode, a reflector 3 to direct the laser beam 4 towards a hair and skin sample and sensor arrangement 5 via a polarisation controller 6. The sensor arrangement 5 of the test rig is configured to measure the amount of energy absorbed by the hair when the laser beam interacts with the hair and thereby determine the attenuation coefficient. The polarisation controller 6 may be a half lambda wave plate which, over the thickness through which the beam passes, will retard unaligned components of the waves to rotate the waves into a uniform polarisation. The polarised beam 10 then passes through a spatial filter 7 to remove aberrations caused by imperfect, dirty or damaged optical equipment. After passing through the spatial filter 7 the polarised laser beam 10 will have a single transverse mode, meaning that the electrical field components of the waves have a uniform and fixed orientation as the beam propagates. A beam expander 8 then expands the beam to fill the aperture of a lens 9 which is configured to focus the polarised beam 10 on the hair and skin sample and sensor arrangement 5.

Several different hair types were tested, as shown in the first column of the results table, to determine the attenuation coefficient for each hair type in two opposing polarisations: firstly when the electric field components were perpendicular to the main hair axis, and secondly when the electric field components were parallel to the main hair axis.

The results of the experiment, shown in Table 1, quantify the difference in attenuation coefficient (units $mm^{-1}$) for the cortex and medulla of different hair types when exposed to light with a wavelength of 830 nm. The first column shows the attenuation coefficients for each of the cortex and medulla portions of hair when the orientation is perpendicular to the main longitudinal axis of the hair (E•). The second column shows the attenuation coefficients when the orientation is parallel to the main longitudinal axis of the hair ($E_{II}$). The attenuation coefficient also depends on the focussing depth of the laser beam, which remained constant during these tests.

TABLE 1

Attenuation coefficients for the cortex and medulla portions of different hair types when the laser beam is orientated differently: $E_{II}$ = parallel, E. = perpendicular. Attenuation coefficients are shown in $mm^{-1}$

| Polarization state | Cortex | | Medulla | |
| --- | --- | --- | --- | --- |
| | E. | $E_{II}$ | E. | $E_{II}$ |
| European blond | 0.22 ± 0.1 | 0.25 ± 0.1 | 75 ± 21 | 79.8 ± 23 |
| European grey | 0.35 ± 0.1 | 0.83 ± 0.3 | 102.9 ± 17 | 114.6 ± 5 |
| European brown | 0.53 ± 0.2 | 1.09 ± 0.1 | 134 ± 40 | 150.9 ± 54 |
| European black | 6.2 ± 0.6 | 7.7 ± 0.7 | 52.3 ± 4.5 | 65.8 ± 12 |
| Indian black | 37 ± 3.8 | 40.8 ± 3.4 | 116.8 ± 38 | 117.2 ± 42 |

The results demonstrate that for each hair type and component of the hair the attenuation coefficient is increased when the electric field components of the electromagnetic waves of the laser beam are orientated to be parallel to the longitudinal axis of the hair.

Therefore, hair can be more effectively severed, with less energy required, when the laser beam is polarised in a parallel manner with respect to the longitudinal axis of the hair. The attenuation can be calculated by considering the loss of intensity during interaction and the intensity transmitted (I) through an object with thickness x is defined as: $I=I_0 e^{-\alpha x}$ where $I_0$ is the incident intensity and · is the attenuation coefficient.

The above defined relationship suggests that the increase in attenuation coefficient demonstrated in Table 1 can reduce the energy required to sever European blond, grey and brown hair by a factor of 2, with improvements also demonstrated for European and Indian black hair.

The optical system demonstrated in the test rig described with reference to FIG. 1 may be adapted for use in a hair cutting device that uses a laser beam, such as a laser shaver. A laser shaver will comprise a laser generator and a polarisation controller and may additionally comprise a lens to focus the laser beam on hairs within a cutting zone, where hairs are received during use. The optical system may also optionally comprise any of: reflective elements, such as mirrors or prisms, to change the direction of the laser beam; filters, such as a spatial filter to remove aberrations and other unwanted interference from the beam; and/or, a beam expander to expand the laser beam to fill a focussing lens.

The device for cutting hair using a laser beam may be formed with a main body and a cutting head that is removable for cleaning, maintenance or replacement. Therefore, the components of the optical system may be located in either the main body or in the removable cutting head. For example, the laser generator and polarisation controller may be located in the shaver body with optical components such as mirrors in the cutting head to direct the laser beam into the cutting zone.

Figure 2:
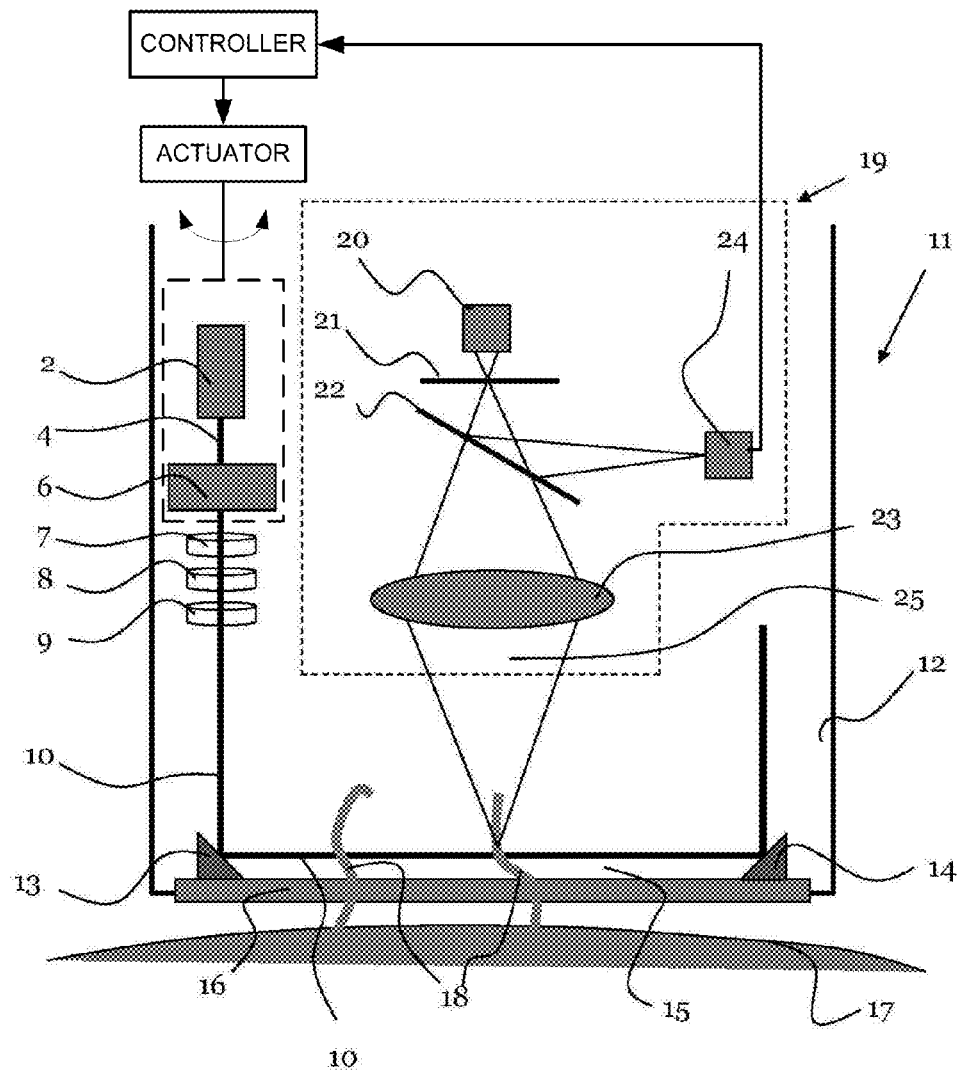
FIG. 2 shows a schematic view of a device for cutting hair using a laser beam with an optical system similar to the optical system of the test rig of FIG. 1.

FIG. 2 shows a schematic diagram of an optical system 11 for a laser shaver including a representation of the body 12 of the device. The optical system is 11 configured to polarise the laser beam for improved hair cutting, as explained above. The optical system 11 is similar to the experimentation rig 1 described with reference to FIG. 1 and comprises a laser generator and a polarisation controller 6. The optical system 11 of the laser shaver shown in FIG. 2 has a laser beam generator 2 that generates a laser beam 4 towards a first reflective element 13 which directs the laser beam across a cutting zone 15 towards a second reflective element 14 that directs the laser beam away from the cutting zone 15 and the skin. The cutting zone is defined in the space between the first and second reflective elements 13, 14. In this example, the laser beam 10 in the cutting zone 15 is positioned parallel to and separated from a hair-skin manipulator 16, which contacts the skin 17 during use to maintain a parallel separation between the skin surface and the laser beam and to manipulate the hairs into a cutting position.

It will be appreciated that the laser beam does not necessarily have to be parallel to the skin during use and may instead be disposed at any angle and may even be targeted towards the skin, at the roots of the hairs below the outermost surface of the skin. Furthermore, the reflective elements are optional; the laser beam generator 2 may instead be disposed in the shaver to direct the laser beam directly towards the cutting zone or the hairs.

The schematic FIG. 2 also shows a filter 7, beam expander 8 and lens 9, which may be the same as described with reference to the test rig of FIG. 1. These components are positioned between the laser beam generator 2 and the first reflective element 13, or alternatively, if no reflective elements are employed, between the laser beam generator and the cutting zone.

The laser beam generator 2 may generate a laser beam 4 within any region of the electromagnetic spectrum but preferably within either the ultraviolet or infrared portions of the electromagnetic spectrum. For example, within the ultraviolet spectrum, the laser beam may have a wavelength of between 200 nm and 500 nm, more preferably between 350 nm and 450 nm. Within the infrared spectrum, the laser beam may have a wavelength of between 2000 nm and 2500 nm, or between 2500 nm and 3500 nm, more preferably between 2575 nm and 3000 nm. Alternatively, the laser beam may have a wavelength of between 200 nm and 900 nm or between 1.5·m and 3.5·m or between 5·m and 10·m. As explained previously, the wavelength may be selected depending on the peak absorption wavelength of the hair type.

The polarisation controller 6 may be configured to alter the polarisation of the laser beam by means of a filter, by filtering out the waves that are not in the desired orientation. Examples of this type of polarisation controller are wire-grid polarisers, absorptive polarisers, reflective polarisers and beam splitting polarisers, any of which are suitable. Filter type polarisers may result in reduced beam energy as some waves are blocked off or absorbed. However, the cutting effectiveness of the laser beam is improved through polarisation because more of the energy of the beam is absorbed by the hair, so the required overall laser beam power may be reduced.

Alternatively, the polarisation controller 6 may be a wave retarder, for example a half-wave plate which retards some components of unaligned waves to rotate and align the waves in a polarised manner. Wave retarding type polarisers have less affect on the beam energy than the filter types and the overall beam energy can be reduced further.

The polarisation controller 6 may be configured to adjust the polarisation orientation, for example by rotating a portion of the polarisation controller or the entire polarisation controller, upon receipt of a command from a controller or a user input. The polarisation controller 6 may be a separate component, as shown in FIG. 2, or it may me integrated with, or be integral to, the laser beam generator so that rotation of the laser beam generator alters the polarisation orientation of the laser beam.

The optional beam expander 8 may be prismatic and expand the beam to fill the focussing lens 9. The spatial filter 7 may alter the laser beam to remove aberrations caused by imperfect, dirty or damaged optical equipment. After passing through the polarisation controller 6 and spatial filter 7 the laser beam 10 will have a single transverse mode, meaning that the components of the waves have a uniform and fixed orientation.

Once the polarised laser beam 10 has passed through the optional beam expander 8 and spatial filter 7 the lens 9 focuses the beam 10 in the vicinity of the hairs 18, within the cutting zone. If reflective elements 13, 14 are used after the beam has passed through the polarisation controller 6 the reflection may result in a change in the orientation of the polarisation and this effect should be accounted for when positioning and orientating the laser beam generator and/or polarisation controller 6.

To determine the optimum polarisation angle relative to the shaver device, the orientation of the hairs 18 as the shaver moves over the skin needs to be considered. It has been determined that the natural angle between the hair and the skin surface typically varies between 27 degrees and 87 degrees. This large range reduces the improvements gained by orientating the polarisation of the laser beam in one fixed orientation at any instant because the laser beam can not be aligned with all of the hairs at the same time. To improve performance, the hair cutting device may include a hair-skin manipulator which is pressed against the skin during use and which manipulates the hairs into a desired orientation relative to the skin as the device is moved over the skin surface. The preferred angle of the hairs relative to the skin will match the orientation of the polarised laser beam and may be, for example, 90 degrees. As shown in FIG. 2, the hair skin manipulator 16 may have a comb protruding from one side that manipulates hairs causing them to stand upright. The hair skin manipulator may instead be a substantially flat plate with a plurality of openings or lamella through which the hairs protrude during use. The hair-skin manipulator could alternatively be a protruding straight edge which is moved over the skin during use and which pushes hairs on the skin into an upright position suitable for cutting with the laser beam.

The optical system may also or alternatively generate multiple laser beam pulses with foci placed close to each other within the cutting zone. The foci may be placed close enough together that there are multiple foci within the diameter of a hair to increase cutting effectiveness. These pulses could be generated from multiple laser beam generators or from a single laser beam generator with a delay which is less than or equal to the thermal relaxation time of hair—the time for hair to return to normal temperature after being heated by a laser beam pulse. In this way, the temperature of the hair will increase until the hair is vaporised and severed.

As explained previously, the optical system 11 for the laser shaver, which polarises the laser beam to align the electric field components with the hair, improves the cutting performance of the device by reducing skin irritation and/or reducing the required power of the laser beam. This is achieved because a higher proportion of the laser beam's energy can be absorbed by the hair, meaning less of the energy will interact with the skin and that the laser beam power may be reduced. Reduced laser beam power will result in increased battery life and reduced damage to optical components. Moreover, the increased efficiency in the cutting process means that the speed at which the device is moved over the skin can be increased without detrimentally affecting the cutting performance. The maximum speed at which the device can be operated while achieving satisfactory cutting performance can be increased.

Also shown in FIG. 2, the hair cutting device may further include a hair detection module 19, as well as the hair-skin manipulator 16 and laser beam generator 2 described previously. The hair detection module 19 may use polarisation resolved confocal imaging, or any other two or three dimensional imaging techniques, to detect the hairs and determine the direction of the main longitudinal axis of those hairs.

The hair detection module shown in FIG. 2 uses polarisation resolved confocal imaging which includes a light source 20, aperture 21, beam splitter 22, lens 23 and detector 24, such as a camera. The arrangement illuminates the cutting zone to be imaged through the aperture 21, which spreads the light into the lens 23 which focuses the light on the cutting zone 15. The beam splitter 22 separates the reflected image for the detector 24. When using polarisation resolved confocal imaging, the hairs 18 need to be brought within the detection cone 25 defined by the light source 20 and aperture 21 to achieve maximum sensitivity (detection of all hairs) and specificity (discrimination between hairs and skin).

The hair detection module 19 allows the angles of the hairs 18 relative to the skin 17 to be determined which gives the optimum angle for the orientation of the polarised laser beam 10. The hair detection module 19 may be configured to determine an average angle for all of the hairs 18 in the cutting zone 15 so that the optimum polarisation orientation angle can be selected. The polarisation orientation may be determined in response to this measurement and may be adjusted by rotating the polarisation controller 6 and/or laser beam generator 2 in response to the determined orientation of the hairs 18 in the cutting zone 15. The device may comprise a controller (not shown) that receives the measurements from the hair detection module 19 and provides control signals to an actuator configured to alter the polarisation orientation.

The laser beam generator may be configured to generate a series of laser pulses with reduced energy. Each individual pulse may not have sufficient energy to sever a hair but the cumulative optical absorption effect will vaporise and sever the hairs. The delay between laser pulses can be determined by considering the thermal relaxation time of hair the time taken for a hair exposed to a laser pulse to return to normal temperature. The inter-pulse time should be less than the temperature relaxation time for hair so that the heat accumulates and increases to the point where the hair is vaporised and severed. The laser pulse arrangement further reduces the energy requirements of the laser beam generator. Furthermore, each reduced power pulse has less interaction with the skin and therefore causes less irritation.

The optical system may also be configured to direct the laser beam across the cutting zone more than one time, thereby creating a multi-pass laser shaver. Multiple laser beams in the cutting zone would increase the cutting effectiveness of the device because fewer hairs would be able to pass through the cutting zone without interacting with, and being severed by, a laser beam. The device may instead comprise a plurality of laser beam generators that direct a plurality of laser beams into the cutting zone and in this case the polarisation orientation of each of the multiple laser beams is controlled to increase the cutting effectiveness. The advantage of having multiple laser beams is that each individual laser beam can have a lower power and the cumulative effect of the multiple beams will cause the hairs to be severed. This reduces irritation of the skin because each individual laser beam would interact less with the skin and generate less heat.

It will be appreciated that the invention as defined in the claims is not limited to a laser shaver device, as described in the above examples, but may instead be easily adapted for use as a trimmer or cutter or any device for cutting hair using a laser beam.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A device for cutting hair using a laser beam, comprising:
   a laser beam generator configured to emit at least one laser beam;
   a polarization controller configured to (i) polarize a whole of the at least one laser beam or (ii) block waves of the at least one laser beam that are in an undesirable orientation direction, so that the polarized whole of the at least one laser beam or non-blocked wave of the at least one laser beam that is in a desirable orientation direction, respectively, that passes through the polarization controller is oriented in a single direction alone for being aligned with a longitudinal axis of a hair to be cut;
   a hair detection module including an optical imaging device configured to detect hair within a cutting zone and determine an orientation of the detected hair within the cutting zone;
   an actuator; and
   a hair detection measurement and polarization orientation altering controller responsive to the determined orientation of the detected hair received from the hair detection module, wherein the hair detection measurement and polarization orientation altering controller provides control signals to the actuator configured to alter the single direction of polarization orientation of the polarization controller to be aligned with the longitudinal axis of the hair to be cut in response to the determined orientation of the hair by the hair detection module, wherein the actuator alters the single direction of polarization orientation of the laser beam by rotating the laser beam generator and the polarization controller.

2. The device of claim 1, wherein the polarization controller is configured to orientate the polarization of the laser beam such that the orientation of an electric field component of the laser beam is substantially parallel to the longitudinal axis of the hair to be cut.

3. The device of claim 2, wherein the polarization controller is a half-wave plate.

4. The device of claim 2, wherein the polarization controller comprises a polarizing filter.

5. The device of claim 1, further including a hair-skin manipulator that contacts the skin of a user and manipulates hair into an orientation suitable for cutting as the device is moved over the skin.

6. The device of claim 5, wherein the polarization controller has a fixed position which corresponds to an average hair orientation as the hair-skin manipulator moves over the skin of a user and manipulates hairs.

7. The device of claim 1, wherein the polarization controller is integrated with the laser beam generator.

8. The device of claim 1, wherein the laser beam generator is configured to generate a series of laser pulses.

9. The device of claim 8, wherein the laser beam generator is configured to generate the series of pulses with an inter-pulse delay that is less than a thermal relaxation time for the hair.

10. The device of claim 1, wherein the laser beam generator is configured to operate at an absorption wavelength of a hair to be cut.

11. The device of claim 1, wherein the laser beam generator further comprises a plurality of laser beam generators configured to generate a plurality of laser beams, the polarization of which is aligned with a longitudinal axis of a hair to be cut.

12. A method of using a laser beam to cut hair comprising:
generating, via a laser beam generator, a laser beam;
polarizing, via a polarization controller, the laser beam as a whole of the laser beam or blocking waves of the laser beam, via the polarization controller, that are in an undesirable orientation direction, so that the polarized whole of the laser beam or non-blocked wave of the laser beam that is in a desirable orientation direction respectively that passes through the polarization controller is oriented in a single direction alone for being aligned with a longitudinal axis of a hair to be cut;
detecting, via a hair detection module including an optical imaging device, hair within a cutting zone and determining an orientation of the detected hair within the cutting zone; and
providing, via a hair detection measurement and polarization orientation altering controller responsive to the determined orientation of the detected hair, control signals to an actuator that alters the single direction of polarization orientation of the polarization controller to be aligned with the longitudinal axis of the hair to be cut in response to the determined orientation of the hair by the hair detection module, wherein the actuator alters the single direction of polarization orientation of the laser beam by rotating the laser beam generator and the polarization controller.

13. The method of claim 12, wherein aligning the polarization of the laser beam is such that an electric field component of the laser beam is substantially parallel to the longitudinal axis of the hair to be cut.

* * * * *